United States Patent [19]
Fletcher et al.

[11] 3,938,373
[45] Feb. 17, 1976

[54] METHOD AND APPARATUS FOR TENSILE TESTING OF METAL FOIL

[76] Inventors: James C. Fletcher, Administrator of the National Aeronautics and Space Administration, with respect to an invention of Orval W. Wade, Littleton, Colo.

[22] Filed: June 27, 1974

[21] Appl. No.: 483,858

[52] U.S. Cl. ............................ 73/95; 73/103
[51] Int. Cl.² .................. G01N 3/28; G01N 3/08
[58] Field of Search ........................ 73/95, 103

[56] References Cited
UNITED STATES PATENTS

| | | | |
|---|---|---|---|
| 1,219,593 | 3/1917 | Scott | 73/103 |
| 2,748,597 | 6/1956 | Kooistra | 73/103 |
| 2,751,512 | 6/1956 | Reen et al | 73/103 |

OTHER PUBLICATIONS

A. Lawley et al., Preparation and Tensile Testing of Thin Metal Foils of Rolled Material, Rev. of Sci. Inst., Vol. 33, No. 11, pp. 1178–1180, Nov. 62.

D. K. Wilsdorf et al., et al., New Tensile Testing Machine for Thin Specimens, Rev. of Sci. Inst., Vol. 33, No. 9, pp. 930–933, Sept. 62.

*Primary Examiner*—James J. Gill
*Assistant Examiner*—Anthony V. Ciarlante
*Attorney, Agent, or Firm*—Howard J. Osborn; John R. Manning

[57] ABSTRACT

Accurate, reproducible results in the tensile testing of thin metal foils are obtained by a method which comprises before placing the test specimen in a tensile testing machine, working the side edges of the test specimen until the edges are parallel and flaw-free, aligning the work specimen between spaced grip end members, securing end portions of the aligned test specimen to the grip end members, each of said grip end members containing female member means in face-to-face relationship to each other. The female member means are located on either side of and perpendicular to the plane of the test specimen and couple with corresponding male member means secured to the jaws of the tensile testing machine.

An aligning apparatus employed in the method of the invention comprises an alignment box having a longitudinal bottom wall and two upright side walls, first and second removable grip end members disposed at each end of said box and means for securing the grip end members within the box. The grip end members are provided with means for receiving opposite end portions of the test specimen and for aligning the test specimen and also with the aforementioned female member means for receiving male member means.

9 Claims, 8 Drawing Figures

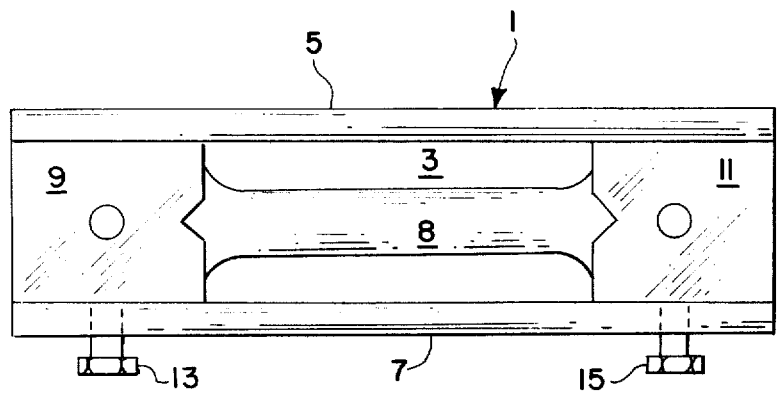
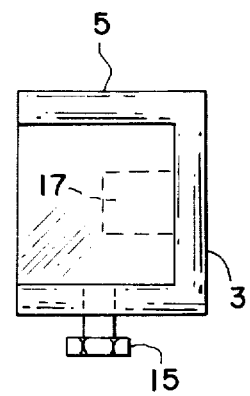
FIG. 1　　　　　　　　FIG. 2
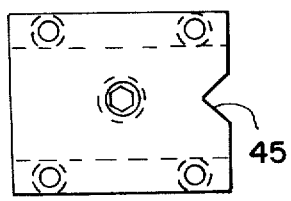
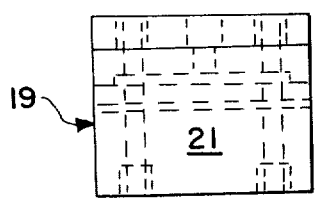
FIG. 3
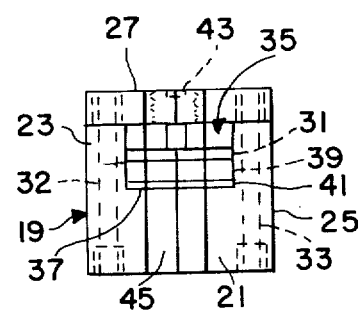
FIG. 5

METHOD AND APPARATUS FOR TENSILE TESTING OF METAL FOIL

ORIGIN OF THE INVENTION

The invention described herein was made in the performance of work under a NASA contract and is subject to the provisions of Section 305 of the National Aeronautics and Space Act of 1958, Public Law 85-868 (72 STAT. 345; 42 U.S.C. 2457).

BACKGROUND OF THE INVENTION

1. Field of the Invention

This invention relates to an improved method for the tensile testing of metal foil specimens and to an aligning apparatus for use in the method.

2. Description of the Prior Art

In the strength of material testing of any specimen the ultimate goal is the acquisition of accurate and reproducible results. The achievement of this goal in the testing of thin metal foil specimens, however, has proved very difficult for more often than not, the results of the testing have been erratic and unreliable. Moreover, the severity of the problem has increased in recent years since advances in structural design are permitting the use of thinner metal coverings useful, for instance, as rocket booster skins. The extreme surface to volume ratio of these thin foils has only aggravated the problem and made achievement of consistent and accurate tensile values all the more difficult.

Numerous techniques have been advanced in the prior art as solutions to these problems. None, unfortunately, have proved completely satisfactory.

SUMMARY OF THE INVENTION

Thus, one object of the invention is to provide a method for obtaining more consistent and accurate strain/stress values in the tensile testing of thin metal foils.

Another object of the invention is to provide a method which avoids premature failure in tension on testing of thin metal foil specimens and the production of a more uniform tension across the specimen cross-section.

Yet another object of the invention is to provide an aligning apparatus for use in the method of the invention. A further object of the invention is to provide an aligning apparatus that does not require elaborate modification to existing equipment and that can be easily adapted to any tensiile testing machine.

These and other objects of the invention are obtained by a method which comprises before placing the test specimen in a tensile testing machine, working the side edges of the test specimen until the edges are parallel and flaw-free, aligning the worked specimen between spaced grip end members, securing end portions of the aligned test specimen to said grip end members, each of said grip end members containing female member means in face-to-face relationship to each other, said female member means being located on either side of and perpendicular to the plane of said test specimen, coupling each of said female member means to corresponding male member means secured to the jaws of said tensile testing machine.

It has been discovered, after considerable study and investigation that perhaps the most critical factor in obtaining reproducible, accurate results is the edge of the test specimen in the reduced area. Any slight flaw, be it a scratch, nick, dent, etc. to the edge can initiate premature failure. In fact, the effect of the defect can be so subtle that the test will appear normal in all respects.

The second most critical factor in obtaining more consistent and accurate results has been found to be the alignment of the specimen in the jaws of the tensile machine. If the specimen is not precisely aligned, it will fail by "tearing" rather than by pure tension. Again the results of a test where the specimen is not properly aligned may be very misleading since they may appear normal in all respects, except the strength and elongation values obtained will be low. The method of the invention utilizes a special aligning means for effecting the necessary alignment.

The aligning apparatus employed in the improved method of the invention constitutes another aspect of the invention and comprises an alignment box comprising a longitudinal bottom wall and two upright side walls integral with said bottom wall, a first removable grip end member disposed at one end of said alignment box between said upright sides, a second removable grip end member disposed at the opposite end of said alignment box, a first means for securing said first grip end member within said box, a second means for securing said second grip end member within said box, said first and second grip end members being provided with means for receiving opposite end portions of the test specimen and for aligning the test specimen parallel to the sides of said grip end members adjacent the upright sides of said box, said first and second grip end members each having on the sides facing each other female member means for receiving male member means, each of said female member means being located on either side of and perpendicular to the plane of said test specimen.

Yet another aspect of the invention comprises the aforementioned grip end members with test metal foil aligned and secured therebetween in combination with male member means for each of the female member means of the grip end members.

DESCRIPTION OF THE DRAWING

In the accompanying drawing several preferred embodiments are shown by way of illustration. In the drawing:

FIG. 1 is a plan view of the aligning box and grip end members disposed therein with the tensile specimen secured therebetween.

FIG. 2 is an end view of the apparatus shown in FIG. 1 with the grip end members removed.

FIG. 3 is a side view of a grip end member employed in the invention.

FIG. 4 is a top view of the grip end member shown in FIG. 3.

FIG. 5 is an end view of the grip end member shown in FIG. 3.

DETAILED DESCRIPTION OF THE INVENTION

Figure 6:
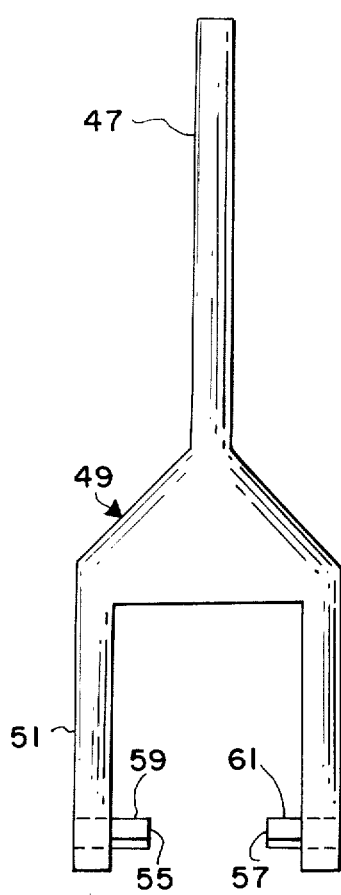
FIG. 6 is a front elevational view of a preferred male member means for coupling with the female member means of the grip end member shown in FIGS. 3–5.

Any working operation or combination of operations may be employed to satisfy the first criteria of the invention that is the preparation of a test specimen having parallel edges that are essentially "flaw-free". By essentially "flaw-free" as used in this specification and in the appended claims is meant having no imperfections or flaws in the edge visible to the naked eye.

The following procedure represents a preferred method of preparing a test specimen with essentially flaw-free edges:

A metal foil specimen, say of 21-6-9 Stainless Steel less than 0.005 in/thick is sheared to ⅝ inch by 10 inch. On the same set up there are sheared aluminum shims 0.010 – 0.015 thick to ⅝ inch. It is important that the shear cut be clean, that is, devoid of nicks and dents and that the shims and specimen match identically so that they will stack exactly. The specimen and shims are then stacked, alternating each, with the shims being outermost in the completed pile. The stack is positioned in a tensilekut fixture and the components of the stack are aligned parallel to one edge and the hold down bolt then tightened. Using a "Tensilekut" machine, the specimen is machined down to the desired width and small increments, not to exceed 0.005 inch per pass. As the final dimension is approached, the feed is reduced to 0.003 inch and the specimen is climb cut in order to get a smooth edge. In this process the specimen is left on the fat side in order to allow for some removal of material during the dressing operation that follows. Generally, 0.505 – 0.508 inch is satisfactory. The pack is then removed from the jig and the specimen separated from the shims. The shims are discarded and the edge of the specimen is run along a 600 grit, 3 inch or larger drum sander.[1] It is essential that this latter operation be conducted utilizing continuous, full strokes, in order to preserve the contour established from the Tensilekut jig and to prevent undercutting caused by non-uniform sanding. One or two passes is ordinarily sufficient to remove the machine marks.

[1] Drum sander was not used. Specimens were finished by hand as identified in amended procedure submitted to Martin Marietta Corp.

The dressing is then continued by hand sanding, with fine crocus cloth. Once again, if the previous steps have been done correctly, a few strokes is all that is necessary to produce an edge that is completely free from burrs, nicks or other flaws. The dimensions are then taken and the two inch gauge mark supplied. Care should be taken to assure no damage is caused by either of these processes.

Alignment of the specimen utilizing the novel alignment apparatus of the invention in order to provide uniform stress across the specimen will now be described with reference to the accompanying drawings.

Referring to FIG. 1, into an alignment box indicated generally as 1 comprised of a base 3 and two upright sides 5 and 7 is disposed at each end thereof grip end members 9 and 11. The grip end members 9 and 11 are secured within the alignment box 1 by means of screw members 13 and 15, respectively. To assist in the alignment of tensile specimen 8, the alignment box 1 is preferably provided with a built-in member 17, as shown in FIG. 2, located on the base of the alignment box 1 intermediate the grip end members 9 and 11.

FIGS. 3 through 5 illustrate in greater detail the grip end member of the invention. Each grip end member is comprised of a main body indicated generally as 19 which is comprised of a rectangular base portion 21 and two upright side portions 23 and 25 integral with the base portion 21. Overlying the main body 19 and resting on the two upright side portions 23 and 25 is a top portion 27 which is secured to the main body portion by screw means 32 and 33. Thus, the main body 19 and the top portion 27 together form a unit having a cavity 35 which includes a base portion 37 onto which the test specimen is inserted. The base 37 of the cavity 35 is generally at a depth which is substantially at midway between the top and bottom of the unit comprised of the main body 19 and the top 27 attached thereto. Above the base 37 there is disposed a rigid pressure plate 39 so as to provide a slot opening 41 for insertion of the test specimen end. Overlying the rigid pressure plate 39 is a flexible pressure plate 31. Extending through the top portion 27 is a socket head set screw 43 for actuating the flexible pressure plate 31 and the rigid pressure plate 39. Down the side of the main body 19 and the top portion 27 there is provided a wedge-shaped female member means 45 which virtually bisects slot opening 41 and extends perpendicularly on either side thereof for receipt of a male member means.

Figure 7:
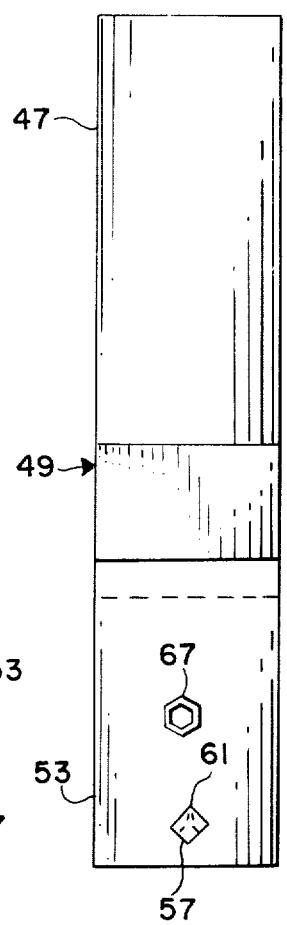
FIG. 7 is a side view of the male member means shown in FIG. 6.

FIGS. 6 and 7 describe a grip end holder which is a male member of a knife edge system for coupling with the wedge shaped female member described above. The grip end holder of FIGS. 6 and 7 comprises a handle portion 47 and a two prong fork portion indicated generally as 49 integral with said handle portion 47. The ends 51 and 53 of fork portion 49 include inwardly projecting male members 55 and 57 each of which contain knife edges 59 and 61 located in a common plane. The distance between the ends of the projecting male members 55 and 57 is slightly less than the distance between the sides of grip end members 9, 11 transverse to the flat plane of the test specimen. The knife edges 59 and 61 cooperate with the wedge shaped female members on either side of and equidistant from the tensile specimen when the ends thereof are positioned in slot opening 41.

Figure 8:
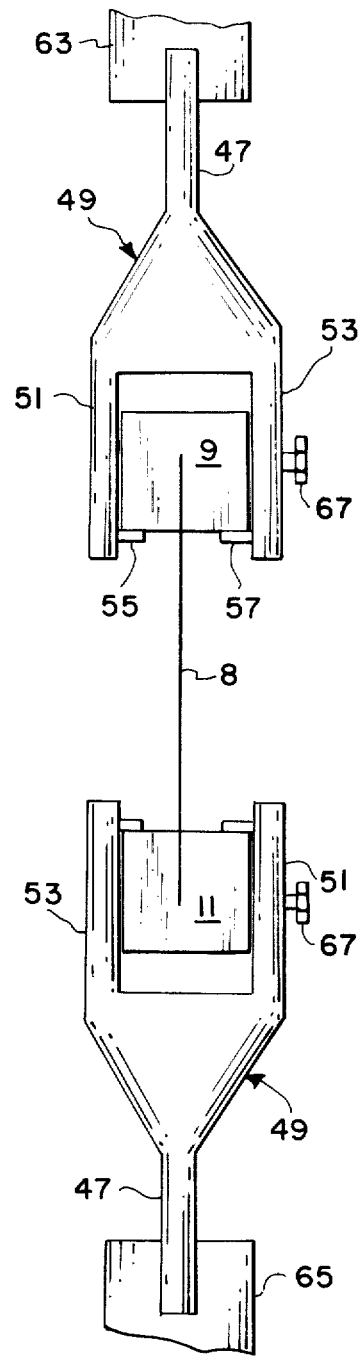
FIG. 8 is a perspective view of the test specimen attached to the jaws of a tensile testing machine ready for testing.

In operation of the aligning apparatus of the invention, the grip end members 9 and 11 are first disposed at either end of the aligning box 1 and secured thereto by screw members 13 and 15, respectively. A tensile specimen whose edges have been rendered flaw-free as described above is then laid on built-in aligning member 17 of the alignment box 5 and inserted into the respective slot openings 41 of the grip end members 9 and 11. The socket head set screw 43 in grip end members 9 and 11 is tightened to actuate flexible pressure plate 31 which in turn actuates rigid pressure plate 39 to secure the ends of the tensile test specimen to the respective grip end members 9 and 11. Screws 13 and 15 are then loosened and the tensile specimen together with end members 9 and 11 between which it is aligned is removed and placed in the grip end holders 49 and locked therein by bolts 67. Grip end holders 49 were previously secured in alignment opposite each other in the jaws 63 and 65 of a tensile testing machine (not shown) as illustrated in FIG. 8. When so positioned the knife edges of the respective male and female members enable the immediate uniform distribution of stress throughout the reduced section of specimen on application of load.

Preferably a smal preload, about 2-5 pounds is first applied and the alignment rechecked. If any misalignment is noted, the specimen is re-positioned. After the specimen has been satisfactorily positioned and preloaded,[2] an extensometer is attached. Once again, great care should be employed to preclude any damage to the edge of the specimen. The specimen is then pulled at a strain rate of 0.005 inch per minute. The specimens should break in the middle third of the gauge length. Any deviation from this pattern should be viewed with caution especially if the values are low. Finally, the results are calculated.

[2] After the specimen has been satisfactorily positioned and preloaded, locking screws shown in an amended drawing of the Clevis holders which fit into the grips of the testing machine are tightened against the specimen gripping members thus providing and preserving proper specimen alignment throughout the test.

While the invention has been described in detail with respect to certain now preferred examples and embodiments of the invention, it will be understood by those skilled in the art after understanding the invention that various changes and modifications may be made without departing from the spirit and scope of the invention, and it is intended, therefore, to cover all such changes and modifications in the appended claims.

What is claimed as new and desired to be secured by Letters Patent of the United States is:

It is claimed:

1. An aligning apparatus for use in the tensile testing of metal foil specimens which comprises an alignment box comprising a longitudinal bottom wall and two upright side walls integral with said bottom wall, a first removable grip end member disposed at one end of said alignment box between said upright sides, a second removable grip end member disposed at the opposite end of said alignment box, a first means for securing said first grip end member within said box, a second means for securing said second grip end member within said box, said first and second grip end members being provided with means for receiving opposite end portions of the test specimen and for aligning the test specimen parallel to the sides of said grip end members adjacent the upright sides of said box, said first and second grip end members each having on the sides facing each other female member means for receiving matching male member means; each of said female member means being in a plane located on either side of and perpendicular to the flat plane of the specimen and parallel to the sides of the grip end members.

2. The apparatus of claim 1 wherein said means in each grip end member for receiving opposite end portions of the test specimen is a slot.

3. The apparatus of claim 2 wherein each grip end member comprises a main body comprising a rectangular base portion and two upright side portions integral therewith, a top portion overlying said main body to form a slot for insertion of a test specimen end portion and means associated with said top portion for securing the inserted test specimen end portion within the grip end member.

4. The apparatus of claim 3 wherein the means associated with said top portion for securing the inserted end portion of the test specimen comprises a rigid pressure plate, a flexible pressure plate overlying said rigid pressure plate and a screw means in said top portion for actuating said flexible pressure plate and said rigid pressure plate.

5. The apparatus of claim 2 wherein the female means is the female member of a knife edge system and the male means is the male member of a knife edge system, said female member being located perpendicular to and on each side of said slot.

6. The combination of claim 5 wherein the means in each grip end member for receiving said opposite end portions of the test specimen and for aligning the test specimen is a slot.

7. The combination of claim 5 wherein each grip end member comprises a main body comprising a rectangular base portion and two upright side portions integral therewith, a top portion overlying said main body to form a slot for insertion of a test specimen end portion and means associated with said top portion for securing the inserted test specimen end portion within the grip end member.

8. The combination of claim 7 wherein the means associated with said top portion for securing the inserted end portion of the test specimen comprises a rigid pressure plate, a flexible pressure plate overlying said rigid pressure plate and a screw means in said top portion for actuating said flexible pressure plate and said rigid pressure plate.

9. In the tensile testing of thin metal foil specimens wherein the test specimen is attached to the jaws of a tensile testing machine, tension is applied at an increasing rate to the specimen until it breaks and the results calculated, the improvement which comprises before placing said specimen in said machine, working the side edges of the test specimen until the edges are parallel and flaw-free, disposing grip end members at opposite ends of an alignment box comprising a longitudinal bottom wall and two upright side walls integral with said bottom wall, said grip end members containing means for attaching and aligning said grip end member with said test specimen secured therebetween to said jaws of the tensile testing machine, securing said grip end members in said alignment box opposite each other, aligning the test specimen between said grip end members and parallel to the sides of said grip end members adjacent the upright sides of said box, securing the end portions of the test specimen to said grip end members, removing the grip end members from the alignment box with the test specimen secured therebetween, attaching and aligning said grip end members with said test specimen secured therebetween to the jaws of the tensile testing machine.

* * * * *